United States Patent [19]
Nakamura et al.

[11] Patent Number: 6,146,012
[45] Date of Patent: Nov. 14, 2000

[54] DIFFERENTIAL THERMAL ANALYZER

[75] Inventors: Nobutaka Nakamura; Rintaro Nakatani; Ryoichi Kinoshita, all of Chiba, Japan

[73] Assignee: Seiko Instruments Inc., Japan

[21] Appl. No.: 09/232,472

[22] Filed: Jan. 15, 1999

[30] Foreign Application Priority Data

Jan. 19, 1998 [JP] Japan ................................. 10-007881

[51] Int. Cl.$^7$ ................................................. G01N 25/00
[52] U.S. Cl. ................................................. 374/10; 374/11
[58] Field of Search ........................................ 374/10, 11

[56] References Cited

U.S. PATENT DOCUMENTS

| | | | |
|---|---|---|---|
| 3,747,396 | 7/1973 | O'Neill | 374/11 |
| 4,552,465 | 11/1985 | Anderson | 374/179 |
| 4,812,051 | 3/1989 | Paulik et al. | 374/10 |
| 5,152,607 | 10/1992 | Ibar | 374/45 |
| 5,439,291 | 8/1995 | Reading | 374/11 |
| 5,549,387 | 8/1996 | Shawe et al. | 374/10 |

FOREIGN PATENT DOCUMENTS 0030495  3/1977  Japan ................................. 374/10

Primary Examiner—Diego Gutierrez
Assistant Examiner—Lydia M. DeJesus
Attorney, Agent, or Firm—Adams & Wilks

[57] ABSTRACT

The DSC (DTA) signal waveform measured under an experimental heating rate condition is separated into a base line and individual basic peak elements, and the respective activation energies are calculated corresponding to each of basic peak elements separated. A DSC (DTA) signal that should be obtained at an another heating rate is estimated from the data obtained from the experimental heating rate and it is outputted. In this process, the temperature shift caused by heating rate difference is corrected using the values of activation energies obtained.

16 Claims, 1 Drawing Sheet

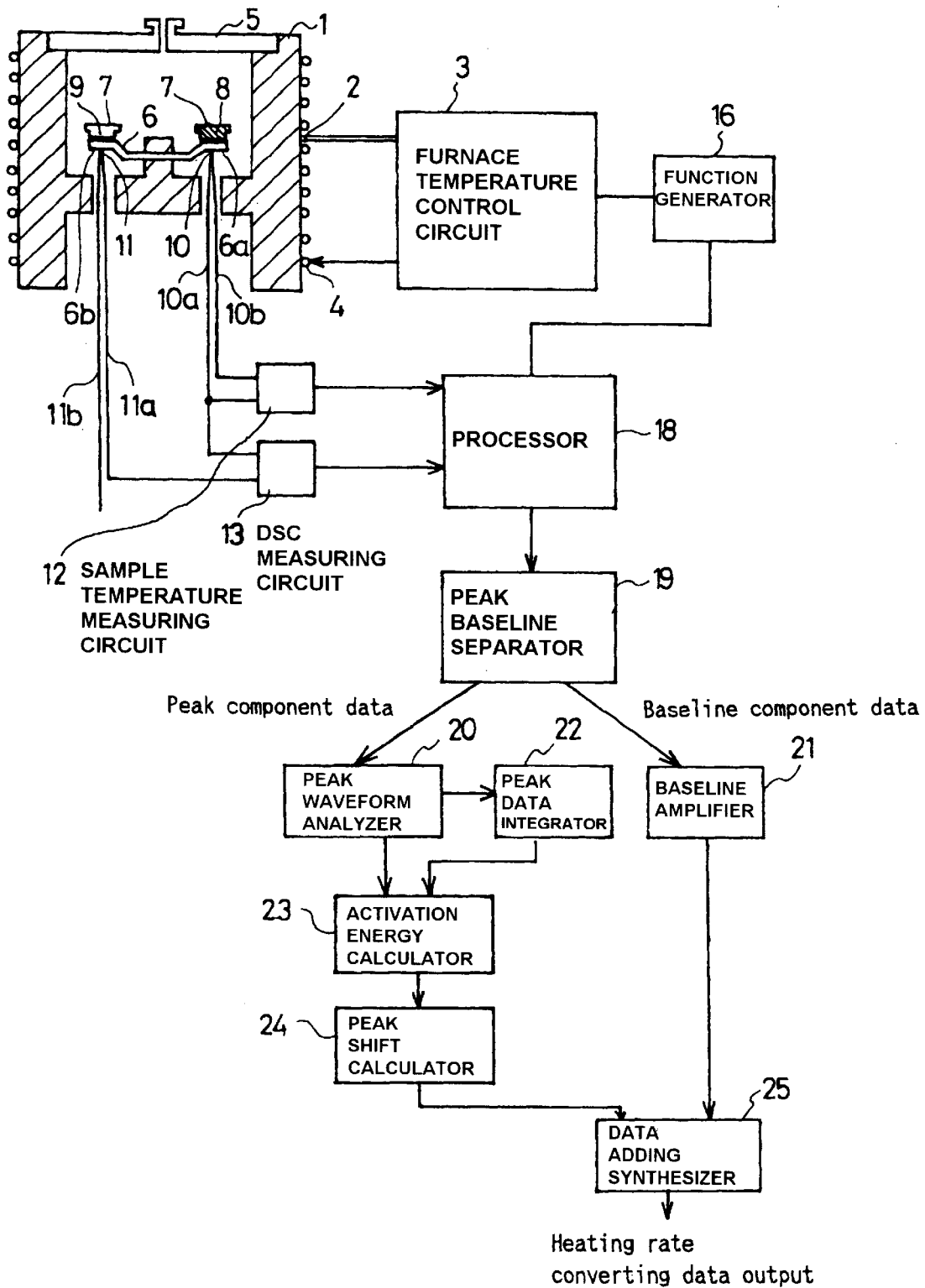

DIFFERENTIAL THERMAL ANALYZER

BACKGROUND OF THE INVENTION

The present invention relates to a thermal analyzer for measuring a signal indicating variations in physical and chemical properties of a sample as a function of sample temperature or time. More particularly, the invention relates to a novel improvement of an apparatus, such as a differential thermal analyzer (DTA) or differential scanning calorimeter (DSC), for measuring the liberation and absorption of heat by a sample, which permits the interchange of thermal analysis data arising from different heating rates of a sample and which, at the same time, allows a thermal analysis of the sample to be performed in a greatly shortened time.

Thermal analysis is an effective means for investigating how material properties vary with temperature. Typical thermal analyzers include differential scanning calorimeters (DSC), differential thermal analyzers (DTA), thermogravimetric measuring apparatuses (TG), thermomechanical analyzers (TMA) and so on, each of which has an objective to measure temperature dependence of various sample quantities of enthalpic balance, differential temperature (qualitative enthalpic balance), weight and length.

In thermal analysis, the physical properties of a sample and temperature variations are continuously measured while heating the sample at a constant rate. In DSC or DTA, heat absorption or liberation in the sample is measured against temperature. The analysis of this kind makes it possible to measure, not only the specific heat of a material, but also the amount of transition heat during fusion or crystallization, and the amount of reaction heat during decomposition or curing, etc.

In the above conventional thermal analysis, it is typical to heat a sample at a heating rate of 5–20 degrees per minute. For example, if a temperature range of about 1000 degrees is scanned, it takes 1 to 3 hours to complete the scan. In this way, the prior art analysis has the disadvantage that the time efficiency is low.

An ordinary thermal analytical apparatus can perform a measuring operation at a heating rate of 50 to 100 degrees per minute, and this shortens the measuring time. Nevertheless, the comparatively low heating rate of 5 to 20 degrees per minute is widely used primarily for the following reason. If a sample inducing plural reactions during scanning of the temperature is heated at a high rate, these reactions tend to overlap. The resulting data is inevitably cumbersome to analyze.

Thermal analysis is intended to investigate the dependence of the physical properties of a sample on temperature. Detailed investigation of the measured signal indicating the physical property has shown that the physical property signal is observed to depend on time as well as on temperature in practice. There are Two main reasons for this, which are:

1) A detector for detecting variations in the physical property of the sample has an intrinsic time constant.
2) The function of temperature is constituted not by a total amount of reactions occurring on a sample but the rate of reaction (reaction ratio per time).

After thermal analysis of a sample is made at a varying heating rate, if measured data are simply taken as physical property values that are functions of temperature, and if they are compared, then results of the measurement are that the same sample shows different decomposition and reaction temperatures reflecting the time dependence effects of the physical property.

SUMMARY OF THE INVENTION

To quickly solve the problems with the prior art technique described above, the present invention has an object of converting an actual-measurement time scale into a time scale expressing a measurement result, thus realizing time-scale conversion based on equations reflecting the relationship between time and temperature.

Specifically, a differential thermal analyzer according to the present invention comprises: means for outputting a sample temperature signal and a differential thermal analysis signal representative of a differential change in temperature difference or heat flow difference of the sample relative to a reference substance by heating the sample and the reference substance at an experimental heating rate, means for separating the differential thermal analysis signal into a peak component and a baseline component, a separator for separating the peak component into a plurality of basic peak elements, an activation energy calculator for calculating an activation energy in accordance with each of the basic peak elements separated by the separator, and a heating rate converter for determining and outputting an estimated differential thermal analysis signal that should be obtained where measuring at a desired heating rate based on the experimental heating rate and the activation energy obtained by the activation energy calculator.

After heating a sample at an experimental heating rate and obtaining an actually-measured thermal analysis signal, a thermal analysis signal that should be obtained at a desired heating rate is estimated from the obtained thermal analysis signal. In this manner, thermal analysis results are obtained under desired heating rate conditions. As a result, measuring time is reduced. The reaction temperature can be compared among different data arising from different heating rates.

BRIEF DESCRIPTION OF THE DRAWINGS

FIG. 1 is a block diagram of a DSC apparatus that is one example of the present invention.

DETAILED DESCRIPTION OF THE INVENTION

An embodiment of the present invention will be explained hereinbelow based on an example shown in the drawing.

In FIG. 1, reference numeral 1 is a silver heat sink having a cross section provided with an almost H-character form. The temperature of the heat sink 1 is measured by a thermocouple 2 for measuring furnace temperature so that a signal thereof is sent to a furnace temperature control circuit 3. An insulator-covered heater 4 is supplied with electric power based on an output of the furnace temperature control circuit 3 so that the heat sink 1 is controlled in temperature through heat conduction. Also, the temperature control of the heat sink 1 employs a known PID control method wherein the heater 4 is supplied with electric power that is calculated, by the furnace temperature control circuit 3, on the basis of proportion, integration and differentiation of the difference between a temperature output from a function generator 16 depending on a desired temperature program and an output temperature of the furnace temperature measuring thermocouple 2.

The heat sink 1 is fixed, at its central portion, with a heat conducting plate 6 of constantan (copper-nickel alloy) in a form that its center is fixed within the heat sink 1. The heat conducting plate 6 is formed, at its one end, with a sample support section 6a in the form of a platform and, at the other end, with a reference support section 6b in a symmetric form.

The sample section 6a has a sample 8 packed in an aluminum vessel 7, placed thereon and the reference section 6b with a vessel 7 packed with alumina powder 9. Also, the heat sink 1 is provided, at its top portion, has placed thereon a lid 5 in an attachable and detachable form so that the vessel 7 can be put in and taken out. A thermocouple junction 10 is formed immediately beneath the sample support section 6a which has a chromel wire 10a as a positive electrode and an alumel wire 10b as a negative electrode. At the junction 10 the temperature of the sample 8 is measured according to an electromotive force of the chromel-alumel (K type) thermocouple. Also, immediately beneath the reference support section 6b is formed a thermocouple junction 11 having a chromel wire 11a as a positive electrode and an alumel wire 11b as a negative electrode. This is provided for the purpose of keeping structural symmetry with respect to the sample support section 6a with heat leak taken into account. The alumina powder 9 as a reference is not directly measured in temperature by the junction 11.

On the other hand, according to the above structure a chromel-constantan thermocouple with a junction 10 as a junction is formed between the constantan as a material of the heat conducting plate 6 and chromel wire 10a. Similarly, at the junction 11 a thermocouple of a similar kind is formed. As a result of this, the voltage between the chromel wire 10a and the chromel wire 11a becomes so-called a differential heat signal representative of a temperature difference between both junctions based on an electromotive force of the chromel-constantan thermocouple.

The chromel wire 10a and the alumel wire 10b are connected to the sample temperature measuring circuit 12. The sample temperature measuring circuit 12 measures, at the junction 10, a temperature of the sample 8 depending on a potential difference between the both wires 10a, 10b.

Also, the chromel wire 10a and the chromel wire 11a are connected to a DSC measuring circuit 13. The potential difference between the chromel wires 10a and 11a represents a temperature difference between the junctions 10 and 11 so that it reflects a temperature difference between the sample 8 and the reference alumina powder 9. At the same time, the potential difference between 10a, 11a also represents heat flows respectively flowing from the sample 8 and the alumina powder 9 into the heat sink 1. That is, it is widely known as a principle of heat flux type DSC that it is possible to handle this potential difference as a differential heat flow signal (DSC signal) if it is appropriately amplified (in a manner taking as a coefficient a thermal resistance in heat flow detection).

In this manner, the sample temperature signal obtained at the sample temperature measuring circuit 12 and the DSC signal obtained at the DSC measuring circuit 13 are both supplied through an analog-digital converter (not shown) to a processor 18 where they are stored.

On the other hand, the temperature of the heat sink 1 can be programmed as a temperature signal in a form of ramp function with respect to time, and is precisely controlled by the action of the furnace temperature control circuit 3 based on an output from a function generator 16 for generating a programmed temperature signal. As a result, the temperature of the sample 8 is controlled according to the heating speed programmed in the function generator 16.

The function generator 16 generates the afore-said temperature program and at the same time is connected to the processor 18 so that it sends an elapsing time after starting measurement as a time signal to the processor 18. The temperature signal from the temperature measuring circuit 12, and the DSC signal from the differential heat flow measuring circuit 13 are supplied to the processor 18, besides the time signal from the function generator 16. The series of signals are controlled as thermal analysis data.

Thermal analysis data is sent from the processor 18 to a peak baseline separator 19 connected to the processor 18. In the peak baseline separator 19, a DSC signal of the thermal analysis data is separated into two components of including a peak component and a baseline component. The peak component data is sent to a peak waveform analyzer 20 connected to the peak baseline separator 19, while the baseline component data is sent to a baseline amplifier 21.

In the peak waveform analyzer 20, peaks are appropriately separated such that the data represented as an overlapping plurality of peaks are each represented as a single peak. Incidentally, where the peak is determined originally as a single peak, no special processing is performed on the data except for passing the data through the peak waveform analyzer 20.

The peak waveform analyzer 20 is connected with a peak data integrator 22 to calculate peak integration data as a time integration for individual peak data after separation. The peak waveform analyzer 20 and the peak data integrator 22 are connected to an activation energy calculator 23. The activation energy calculator 23 calculates an activation energy for each DSC peak from the data of temperature, peak components and peak integration based on a well known method as a Freeman-Carroll method.

The information of the separated DSC peak signal and its temperature range and an activation energy value corresponding to each DSC peak is sent to a peak shift calculator 24 connected to the activation energy calculator 23. In the peak shift calculator 24, in accordance with Arrhenius rule representing a relationship between temperature and time of reaction occurring in the sample, there are calculated temperature deviations at each DSC peak point to be generated where measuring by varying the heating rate based on an activation energy value at each DSC peak to determine individual DSC peaks with the temperature shifted by the deviation amount. At this time, the height (magnitude) of the DSC peak signal is rated by multiplying by an appropriate coefficient so as to maintain the magnitude of the peak integration signal (i.e., in a manner saving a DSC peak are depicted by taking the horizontal coordinate as a time coordinate).

On the other hand, the baseline amplifier 21 amplifies the magnitude of the baseline component so as to be proportional to the heating rate depending on variation in the heating rate.

A data addition synthesizer 25 is connected to the peak shift calculator 24 and the baseline amplifier 21 so that added together at each temperature are the individual DSC peak data from the peak shift calculator 24 and the DSC baseline data from the baseline amplifier 21. The output of the data addition synthesizer 25 thus obtained lies as a presumption on a DSC signal to be obtained by varying the heating rate.

An actual example of measurement performed using the present instrument is next described. A thermally stable reference substance, e.g., an alumina powder 9 contained in an aluminum vessel 7, is placed on the reference section 6b together with its vessel. A sample contained in an aluminum vessel 7 to be subjected to DSC measurement is placed on the sample section 6a together with its vessel 8. A temperature program used for measurement is inputted to the function generator 16. The temperature program sets a start temperature, an end temperature, and a heating rate in the interval between both temperatures. An appropriate temperature program should be used in accordance with sample properties and measurement purposes. The typical prior art example of a temperature program includes a program to heat up from room temperature to 600 degrees at a rate of 10 degrees per minute. If a measurement is executed under this program, it takes about one hour for measurement. The measuring time can be shortened by increasing the heating rate. However, varying the heating rate will change the reaction temperature and separate reactions to a lesser extent. Consequently, it is more difficult to detect the individual reactions. For these reasons, the heating rate used for actual thermal analysis is roughly from 5 degrees to 20 degrees per minute. In the present embodiment, however, the conventional problems can be eliminated by the measurement with increased heating rate due to the functions of the peak baseline separator 19 to the data addition synthesizer 25, and accordingly measurement is carried out using a temperature program a rate of 50 degrees per minute. The respective signals of lapse time, sample temperature and differential heat flow (DSC) in measurement are taken, as a set of thermal analysis data, at a predetermined sampling interval throughout the measurement into the processor 18 through a (not-shown) analog-digital converter.

The thermal analysis data taken into the processor 18 is sent, after ending the measurement, to the peak baseline separator 19. In the peak baseline separator 19, the DSC signal is separated into a peak component and a baseline component by the following procedure.

(1) The second order derivative of the DSC signal with respect to time is calculated while performing appropriate smoothing processing.

(2) It is regarded as a "(DSC) stable region" that a region where the second-order derivative determined in (1) stays between upper and lower thresholds for a given time period or longer.

(3) It is regarded as a "(DSC) peak region" that a region where a condition is satisfied that the second-order derivative signals sandwiched between two adjacent stable regions and directed inward from the opposite stable regions go beyond for the first time the threshold in a same direction (both positive direction or both negative direction).

(4) Straight-line-interpolating the DSC signal values at boundaries of left and right two points between a DSC peak region and the DSC stable region on the respective sides, this is regarded as a "baseline in the peak region".

(5) Connecting DSC signals at DSC stable regions and baselines at respective peak regions in a time order, this is regarded as a "(DSC) baseline component".

(6) A component subtracting the baseline component determined at 5) from the original DSC signal is regarded as a "peak component" (that is, the peak component have a non-zero value only at the peak region).

The peak component data thus obtained is sent to the peak waveform analyzer 20, while the baseline component data to the baseline amplifier 21.

In the peak waveform analyzer 20, first examined are the number of peaks contained in the peak component data signal and the manner of their overlapping. The number of peaks and how they overlap are examined by the following procedure:

(1) The second-order derivative of the peak component signal with respect to time is calculated while performing appropriate smoothing processing.

(2) The second-order derivative signal found in (1) is differentiated with respect to time, thus obtaining a third-order derivative signal.

(3) Each point where the third-order derivative signal is zero and, at the same time, the second-order derivative signal assumes a negative minimum value is taken as a peak position. The number of the peak positions is found.

(4) If plural peak positions are present, and if the DTG signal is zero at every point between the adjacent peaks, the situation is regarded as "no peak overlap". In other cases, the situation is regarded as "overlap of peaks".

(5) If overlap of peaks exists, the peak waveform analyzer 20 separates the individual peaks according to a well-known overlapping waveform-analyzing procedure such as Symplex method or Gauss-Newton Method.

(6) If adjacent peaks overlap, the maximum value of the second-order derivative signal of the peak component signal existing between the peak positions is taken as a "peak boundary". If the adjacent peaks do not overlap, one of the points at which the DTG signal is zero between the adjacent peak is taken as a "peak boundary".

The peak data separated by the peak waveform analyzer 20 is each sent to the peak data integrator 22. In the peak data integrator 22, the peak data is each integrated with respect to time based on the following [Equation 1].

$$X_p(t) = \int_{t_i}^{t} x_p(t') dt' \qquad \text{[Equation 1]}$$

$$t_i \leq t \leq t_f$$

where $x_p$: peak data signal value

Xp: peak integral data signal value t, t': time $t_i$: peak region start time $t_f$: peak region end time In the activation energy calculator 23, activation energy is calculated on the peaks separated by the peak waveform analyzer 20 based on the Freeman-Carroll method by using temperature, peak data and peak integration data.

Applying with logarithm at both sides for the kinetic equation of an n-th order reaction obeying the Arrhenius' Law, obtaining the following [Equation 2].

$$\frac{\Delta \ln(y)}{\Delta \ln(1-x)} = n - \left(\frac{\Delta E}{R}\right) \cdot \frac{\Delta\left(\frac{1}{T}\right)}{\Delta \ln(1-x)} \qquad \text{[Equation 2]}$$

where y: DSC peak signal (=dx/dt)

t: time x: DSC peak integral signal

T: absolute temperature

R: gas constant n: reaction order

ΔE: activation energy

In the above [Equation 2], those other than the activation energy (ΔE) are constants or known data. Accordingly it is possible to determine an activation energy based on the above equation.

Incidentally, those having an activation energy value obtained in the course of calculating an activation energy and exceeding 500 kilo Joules per mole is treated as infinity activation energy due to consideration to the possibility of the first-order phase transition (it is theorized that no temperature deviation occurs in the first-order phase transition even if the heating rate is varied).

In this process, the number of the activation energy obtained agrees with the number of the peaks. Incidentally, it is assumed that the activation energies have values within every time range of the data and takes the form of a step function whose value varies across every peak boundaries.

The kinetics for single reaction is expressed by the following equation of the Arrhnius' law.

$$\frac{dx}{dt} = -A \cdot \exp\left(-\frac{\Delta E}{RT}\right) \cdot g(x)$$ [Equation 3]

where, x is the amount of chemical structure that is created or reduced by the reaction, t is time, A is a frequency factor (constant), $\Delta E$ is an activation energy, R is a gas constant, T is an absolute temperature and g is a function of x.

On the other hand, in thermal analysis whose measurements are made at a given heating rate of B degrees per minute, the following relationship holds between the time t and temperature T.

$$T(t) = a + B \cdot t$$ [Equation 4]

where a is a constant.
Therefore, $$dt = \frac{dT}{B}$$ [Equation 5]

[Equation 5] is substituted into [Equation 3] to separate the variables of x and T. Thus, $$\frac{dx}{g(x)} = \frac{A}{B} \cdot \exp\left(-\frac{\Delta E}{RT}\right) \cdot dT$$ [Equation 6]

Taking the natural logarithm of both sides and rearranging the equation gives rise to [Equation 7].

$$\ln B = -\frac{\Delta E}{R} \cdot \frac{1}{T} + \ln A - \ln\left(\frac{dx}{g(x)}\right)$$ [Equation 7]

[Equation 7] can be interpreted as follows: If the heating rate is $B_1$ degrees/min, per minute, the reaction ratio reaches x at temperature T. Consider a point where the reaction ratio assumes a certain value $x_0$. When the heating rate is $B_1$ degrees/min, the reaction ratio is $x_0$ at a temperature of $T_1$. When the reaction rate is $B_2$ degrees/min, the reaction ratio is $x_0$ at a temperature of $T_2$. The second term of the right side is a constant. If a point where the reaction ratio assumes a given value $x_0$ is taken into account, the third term of the right side is also constant. Let C (constant) be the sum of the second and third terms of the right side. The relation described above is expressed by the following simultaneous equations:

$$\ln B_1 = -(\Delta E/RT_1) + C$$ [Equation 8]

$$\ln B_2 = -(\Delta E/RT_2) + C$$

C is removed from [Equation 8]. Solving them with respect to $T_2$ gives rise to $$T_2 = 1/\{(1/T_1) + (R/\Delta E) \cdot \ln(B_1/B_2)\}$$ [Equation 9]

The equation [Equation 9] indicates that the point of temperature T1 in each peak signal waveform of DSC separated should be shifted to temperature T2 in order to convert thermal analysis data measured at a heating rate B1 into data about heating rate B2.

All the peak waveforms thus obtained are summed up. The whole DSC peak component signal that should be obtained when a measurement is made at the heating rate B2 degrees per minute is estimated.

Further, if the DSC baseline signal after converting the heating rate as an output of the baseline amplifier 21 is added, the total DSC signal that should finally be obtained in the case of the measurement at the heating rate B2 can be estimated.

Although all of the explanations were made using the DSC apparatus in the above embodiment, a similar effect can be obtained by using a DTA apparatus and a similar technique.

On the other hand, it is widely known that the output signal in the DSC apparatus or DTA apparatus is accompanied by a particular signal delay due to thermal detection. Several methods are proposed for correcting such a signal delay based on a well-known deconvolution technique. When these techniques are applied to the output signal processing in the apparatus described in the embodiment, higher quality data can be obtained.

Since the invention is constructed as described thus far, a measurement can be completed in a time that is reduced by a factor of 5 using a DSC or DTA apparatus in accordance with the present invention by performing the measurement at an experimental heating rate of 50 degrees per minute, for example, and then converting data into data that would be obtained at a heating rate of 10 degrees/min. The measuring efficiency can be enhanced by the great reduction in the measuring time.

Furthermore, because the present invention is applicable, after measurement, to a simulation for a DSC (DTA) result in a case of changing a heating rate condition, it can be utilized for a purpose that more precise data analysis is made by selecting the experimental heating rate lower in order to reduce an effect of response delay due to heat flow measurement and converting into higher-rate heating data.

Additionally, in accordance with the invention, data arising from different heating rates during measurement are converted into the same heating rate conditions and data about samples can be compared. Consequently, the reaction temperatures of the samples can be compared precisely in spite of different heating rate conditions.

What is claimed is:

1. A differential thermal analyzer comprising: means for outputting a sample temperature signal and a differential thermal analysis signal representative of at least one of a differential change in temperature difference and a heat flow difference of a sample relative to a reference substance by heating the sample and the reference substance at an experimental heating rate; and processing means for processing the sample temperature signal and the differential thermal analysis signal obtained during thermal analysis of the sample, the processing means including separating means for separating the differential thermal analysis signal into a peak component and a baseline component, an activation energy calculator for calculating an activation energy based on the peak component of the differential thermal analysis signal, and a heating rate converter for calculating an estimated differential thermal analysis signal that would be obtained under a thermal analysis of the sample conducted at a desired heating rate different from the experimental heating rate based on the experimental heating rate and the activation energy obtained by the activation energy calculator, the estimated differential thermal analysis signal that should be obtained at the desired heating rate being calculated based on the differential thermal analysis signal derived from the experimental heating rate.

2. A differential thermal analyzer according to claim 1; further comprising a furnace having a reaction vessel in which the sample and the reference substance are heated; temperature detecting means for detecting a temperature of the sample and the reference substance and outputting the differential thermal analysis signal; and a temperature control circuit for controlling a furnace temperature according to the experimental heating rate.

3. A differential thermal analyzer according to claim 2; wherein the furnace comprises a heat sink having a metallic outer surface defining an internal chamber, a removable cover, a heat conducting plate disposed in the internal chamber having a sample support section provided with a sample platform for supporting the sample to be measured in a first vessel and a symmetrically arranged reference support section having a reference support platform for supporting the reference substance in a second vessel.

4. A differential thermal analyzer according to claim 3; wherein the temperature detecting means comprises a first thermocouple junction formed at each of the sample support section and the reference support section, the first thermocouple junctions each comprising a positive electrode wire formed of a first material attached to the heat conducting plate and a negative electrode wire formed of a second material attached to the heat conducting plate, and a second thermocouple junction formed at each of the sample support section and the reference support section, the second thermocouple junctions each comprising the heat conducting plate and a respective positive electrode wire.

5. A differential thermal analyzer according to claim 4; wherein the reaction vessel is formed of silver, the heat conductive plate is formed of constantan, the positive electrode of the thermocouple junctions formed at the sample support section and the reference support section is formed of chromel and the negative electrode of the first thermocouple junctions is formed of alumel.

6. A differential thermal analyzer according to claim 4; wherein the temperature detecting means further comprises means for measuring the differential thermal analysis signal in response to a difference in electromotive forces produced by the second thermocouple junctions.

7. A differential thermal analyzer according to claim 6; further comprising a function generator for outputting a temperature control signal to the furnace temperature control circuit to control the furnace temperature according to a predetermined temperature control program, and for outputting an elapsed time signal.

8. A differential thermal analyzer according to claim 7; wherein the temperature program comprises a start temperature at which thermal analysis of the sample is to begin, an end temperature at which the thermal analysis is to end, and a temperature rate at which the temperature of the sample is to be increased during the thermal analysis.

9. A differential thermal analyzer according to claim 1; wherein the separating means includes means for separating the differential thermal analysis signal into a peak component and a baseline component by calculating a second order derivative of the differential thermal analysis signal, assigning as baseline regions those regions of the differential thermal analysis signal where the value of the second order derivative does not deviate outside a threshold range for at least a predetermined period of time, assigning as peak regions those regions of the differential thermal analysis signal where the value of the second order derivative deviates outside the threshold range, and subtracting the baseline regions of the differential thermal analysis signal from the original differential thermal analysis signal to obtain the peak component.

10. A differential thermal analyzer according to claim 1; wherein the processing means further comprises a separator for separating the peak component into a plurality of peak elements and outputting peak data.

11. A differential thermal analyzer according to claim 10; wherein the separator comprises differentiating means for taking the second-order derivative and a third-order derivative of the peak component with respect to time, assigning as a peak position of the differential thermal analysis signal each point at which the third-order derivative of the peak component is equal to zero and, at the same time, the second-order derivative signal has a negative minimum value, counting the number of peak positions and separating overlapping peaks using an overlapping waveform-analyzing procedure.

12. A differential thermal analyzer according to claim 10; further comprising a peak data integrator for integrating the peak data with respect to time to produce peak integration data.

13. A differential thermal analyzer according to claim 12; wherein the activation energy calculator includes means for calculating the activation energy of the peaks separated by the separator based on the temperature, peak data and peak integration data.

14. A differential thermal analyzer according to claim 1; wherein the heating rate converter comprises a peak shift calculator, a baseline amplifier and a data adder.

15. A differential thermal analyzer according to claim 1; wherein the reference substance is alumina.

16. A differential thermal analyzer comprising: means for outputting a sample temperature signal and a differential thermal analysis signal representative of at least one of a differential change in temperature difference and a heat flow difference of a sample relative to a reference substance by heating the sample and the reference substance at an experimental heating rate; and processing means for processing measured data obtained during the thermal analysis, the processing means including separating means for separating the differential thermal analysis signal into a peak component and a baseline component, a separator for separating the peak component into a plurality of peak elements, an activation energy calculator for calculating an activation energy for each of the respective peak elements separated by the separator, and a heating rate converter for calculating an estimated differential thermal analysis signal that would be obtained under a thermal analysis of the sample conducted at a desired heating rate different from the experimental heating rate based on the experimental heating rate and the activation energy obtained by the activation energy calculator, the estimated differential thermal analysis signal that should be obtained at the desired heating rate being calculated based on the differential thermal analysis signal derived from the experimental heating rate.

* * * * *